United States Patent [19]
Clemens et al.

[11] Patent Number: 6,001,075
[45] Date of Patent: Dec. 14, 1999

[54] DYNAMIC SPLINT

[75] Inventors: Leonard M. Clemens, Port Orange, Fla.; William T. Rembold, Cincinnati, Ohio; Dennis L. Ashford, Dayton, Ky.

[73] Assignee: EX. P.H., Dayton, Ky.

[21] Appl. No.: 08/989,379

[22] Filed: Dec. 12, 1997

[51] Int. Cl.⁶ .................................................... A61F 5/00
[52] U.S. Cl. ................... 602/16; 602/20; 602/26
[58] Field of Search ................... 602/5, 16, 20, 602/21, 23, 26; 601/23, 33

[56] References Cited

U.S. PATENT DOCUMENTS

| | | |
|---|---|---|
| 76,382 | 4/1868 | Barnes . |
| 282,650 | 8/1883 | Baron . |
| 1,196,887 | 9/1916 | Saemann . |
| 2,883,982 | 4/1959 | Rainey . |
| 4,433,679 | 2/1984 | Mauldin et al. . |
| 4,508,111 | 4/1985 | Hepburn . |
| 4,538,600 | 9/1985 | Hepburn . |
| 4,633,867 | 1/1987 | Kausek et al. . |
| 4,718,665 | 1/1988 | Airy et al. ............................ 602/16 X |
| 4,856,500 | 8/1989 | Spademan . |
| 5,025,782 | 6/1991 | Salerno . |
| 5,036,837 | 8/1991 | Mitchell et al. . |
| 5,036,839 | 8/1991 | Mitchell et al. . |
| 5,116,296 | 5/1992 | Watkins et al. ....................... 602/26 X |
| 5,213,094 | 5/1993 | Bonutti . |
| 5,328,446 | 7/1994 | Bunnell et al. ........................... 602/16 |
| 5,358,468 | 10/1994 | Longo et al. ............................ 601/33 |
| 5,358,469 | 10/1994 | Patchel et al. . |
| 5,399,154 | 3/1995 | Kipnis et al. . |
| 5,437,619 | 8/1995 | Malewicz et al. . |
| 5,472,410 | 12/1995 | Hamersly . |
| 5,472,412 | 12/1995 | Knoth . |
| 5,490,831 | 2/1996 | Myers et al. . |
| 5,520,625 | 5/1996 | Malewicz . |
| 5,520,627 | 5/1996 | Malewicz . |
| 5,571,078 | 11/1996 | Malewicz ................................ 602/27 |
| 5,722,937 | 3/1998 | Smith ..................................... 601/23 |
| 5,759,165 | 6/1998 | Malewicz ................................ 602/21 |

OTHER PUBLICATIONS

Brochure—"Ultraflex: The Next Generation in Dynamic Splits", Empi, Inc., St. Paul, Minnesota 55112.
Brochure—"Reduce Your Patients' Difficult Contractures . . . ", DynaSplint Systems, Inc., Baltimore, Maryland 21227.
Brochure—"Pro-glide", Dynamic ROM Wrist Orthosis, Staodyn, Inc.
Magazine ad—"Advance Dynamic ROM Splints" by Emp, Inc., St. Paul, Minnesota 55112; REHAB Management, Feb./Mar. 1995.

*Primary Examiner*—Jeanne M. Clark
*Attorney, Agent, or Firm*—John M. Harrison

[57] ABSTRACT

A dynamic splint for a joint of a limb undergoing rehabilitation. The splint having a pair of elements each comprising a first tubular strut, a second lever-like strut and an intermediate gear housing mounted on one end of the first strut. A first toothed gear is rotatively mounted on a first shaft in the gear housing and is located adjacent the first strut. A second cooperating toothed gear is rotatively mounted on a second shaft in the gear housing adjacent the second strut. The first gear is missing at least one tooth. The second gear is missing a plurality of teeth in a row. The second strut is pivoted to the second shaft and is attached to the second gear at one of a plurality of selectable positions thereabout. A cam wheel is rotatively mounted on the first shaft and is affixed to the first gear. A compression spring is mounted in the tubular first strut. A cable is affixed at one end to the cam wheel and is operatively adjustably affixed to the spring. The cam wheel is so configured that the assembly of the spring, cable, cam wheel and first gear apply an adjustable constant torque in one of a clockwise or counterclockwise direction to the second gear and second strut only when the teeth of the gears are meshed. The second strut and second gear are rotatable throughout the normal range of motion. The gears are meshed only in the passive portion of the normal full range of motion of the joint as determined by the attachment position of the second strut on the second gear.

20 Claims, 9 Drawing Sheets

DYNAMIC SPLINT

TECHNICAL FIELD

The invention relates to a dynamic splint, and more particularly to such a splint which applies a constant, pre-adjusted torque across a hinged joint undergoing rehabilitation. The application of the constant torque being limited to the shortened muscle group within some or all of the non-active part of the full range of motion of the joint.

BACKGROUND ART

As indicated above, the dynamic splint of the present invention is applicable to various hinged joints such as the finger, elbow, wrist, shoulder, hip, knee, ankle and toe joints. It will, for purposes of illustration, be described in its application to an elbow joint, although its use is not intended to be so limited.

In the case of an arm or elbow fracture or break, the arm is set and provided with a cast. Normally the cast immobilizes the arm in a bent condition generally at about 45 degrees. When the cast is ultimately removed, it is usually found that the flexion muscle group over time has been partially absorbed and thus has been shortened. At the same time, the opposition muscle group (i.e. the extension muscle group) has been stretched, causing it to grow longer. The flexion muscle group, when stretched by the extension muscle group (which is contracting), is not long enough to allow full extension of the arm. The term "contracture" is often used to define this condition. Similarly, since the extension muscle group has elongated, it cannot contract enough to fully extend the arm. As a result of this, the patient loses part of the normal active range of movement, say from about 40 degrees or 20 degrees to +15 degrees, as will be further explained hereinafter.

In recent years, attention has been turned to dynamic splints. This is based upon the belief that a constant dynamic low intensity stress to remodel contracted and scarred connective tissue may be more efficient and safer than traditional range-of-motion exercises and passive stretching by a therapist. A constant state of tension appears to trigger and optimize the remodeling process, a process which may be home-based rather than clinic-based.

Laboratory studies show that the best way to permanently lengthen contracted connective tissue, without compromising its structural integrity, is by prolonged low intensity stressing (stretching). Tests further show that contracted connective tissue, when continuously stretched at a constant low intensity force (in the form of torque), remodels more rapidly, requiring less rehab time and less cost.

While showing promise, present day dynamic splints have several major drawbacks. Most dynamic splints cannot maintain a constant force (torque) without frequent adjustment. The adjustments must be correctly made or the benefits of the splint are geatly diminished. If improperly made, the adjustments may result in ineffective torque levels, that may damage fragile tissue, cause pain, prolong rehabilitation, and may interfere with or inhibit the normal function of the extremity.

As indicated above, patients with a range-of-motion loss have a range of loss which is simply a part of the overall normal range of movement of the limb (in this instance an arm). Thus, the patient has, with respect to the normal over-all range of motion, an active range through which he can move his arm and a passive range through which he cannot move his arm. Clinical efforts would be targeted at the passive range, only, but prior art dynamic splints have not been capable of doing this. Prior art dynamic splints provide torque over a predetermined range of motion, dictated by the nature of the mechanism of the splint. Prior art splints do not discriminate between the active and passive ranges within the over-all range of motion. As a result of this, the splint may provide a passive assist to active muscle activity which may impair the normal muscle activity which the patient already has, and which may interfere with or inhibit the absorption of adaptively lengthened muscle and thus prolong and complicate the recovery process. The splint may also trigger unwanted neurological response which may inhibit extremity use and use of the splint, further complicating recovery.

It is an object of the present invention to provide a dynamic splint which creates within the passive zone a torque to influence the synthesis of new tissue with respect to the contracted muscle group. It keeps the contracted tissue in a constant state of mild tension within the passive range of motion, so that cells multiply and proliferate in response to the need created by the mild stress applied by the splint. The range of torque can be adjusted depending upon the application of the splint.

It is an object of the present invention to provide a dynamic splint which will not supply a passive assist to the stretched extension muscle group, retarding its partial absorption or shortening and thereby impeding the achievement of a normal range of movement.

It is an object of the present invention to provide a dynamic splint which will apply torque only in the targeted treatment range (i.e. the passive range) of the overall normal range of movement.

It is an object of the present invention to provide a dynamic splint which will supply a constant therapeutic torque only to the contracted muscle group, and only within its passive range.

It is an object of the present invention to provide a dynamic splint the constant therapeutic torque of which can be easily and accurately adjusted.

It is an object of the present invention to provide a dynamic splint, wherein the adjustable constant torque is supplied by a spring and a dedicated cam, together with a pair of gears.

It is an object of the present invention to provide a dynamic splint which, when used in association with an orthopedic or neurological malady, can have the amount of torque it applies and the passive range over which it applies the torque easily adjusted to minimize or eliminate problems of spasticity and/or tissue trauma.

It is an object of the present invention to provide the dynamic splint with a pivotable distal cuff member.

It is an object of the invention to provide a dynamic splint which, when located within the active zone, can be easily adjusted and easily applied and removed without having to lock the splint.

It is an object of the present invention to provide a dynamic splint which can be used in lieu of range-of-motion exercises and actual stretching techniques.

It is an object of the present invention to provide a dynamic splint which can be used in orthopedic areas and non-orthopedic areas such as stroke, multiple sclerosis, cerebral palsy, burns and the like.

It is an object of the present invention to provide a dynamic splint which can be locked to form a rigid immobilizing splint.

It is an object of the present invention to provide a dynamic splint with means to lock the spring and eliminate the application of torque.

It is an object of the present invention to provide a dynamic splint which is nice looking, compact, lightweight, of simple construction, inexpensive to manufacture, easily applied, easily adjusted, easily removed and comfortable.

It is an object of the present invention to provide a dynamic splint of such nature that a patient will willingly comply to the requirements of its use.

DISCLOSURE OF THE INVENTION

According to the invention there is provided a dynamic splint for a joint of a limb undergoing rehabilitation. The dynamic splint has a pair of elements, each comprising a first tubular strut attached to a gear housing and a second lever-like strut having an end mounted within the gear housing. A first toothed gear is rotatively mounted in the gear housing on a first transverse shaft and is located adjacent the first strut. A second cooperating tooth gear is rotatively mounted on a second transverse shaft in the gear box adjacent the second strut. The first gear is missing at least one tooth while the second gear is missing a plurality of teeth in a row.

The second strut end located within the gear housing, is pivoted to the second shaft, and is spaced from the second gear by a spacer. The second strut is attached to the second gear at any one of a plurality of selectable positions thereabout by a pin. A cam wheel is rotatively mounted on the first shaft and is affixed to the first gear. A compression spring is mounted in the first tubular strut. A cable is affixed at one of its ends to the cam wheel, and is operatively and adjustably affixed at the other of its ends to the compression spring. The cam is so configured that the assembly of the spring, the cable, the cam and the first gear apply an adjustable constant torque to the second gear and the second strut, only when the teeth of the first and second gears are meshed. The second strut and the second gear are rotatable throughout the normal range of motion of the joint being treated. The gears are meshed only in the patient's passive range portion of the normal range of motion. This is achieved by the attachment position of the second strut on the second gear as will be apparent hereinafter. The second strut is spaced from the second gear by an amount such that the cam wheel will not interfere with the motion of the second strut. The first tubular struts carry a full cuff therebetween. The second struts may carry a hammock-type half cuff therebetween.

DETAILED DESCRIPTION OF THE INVENTION

Figure 1:
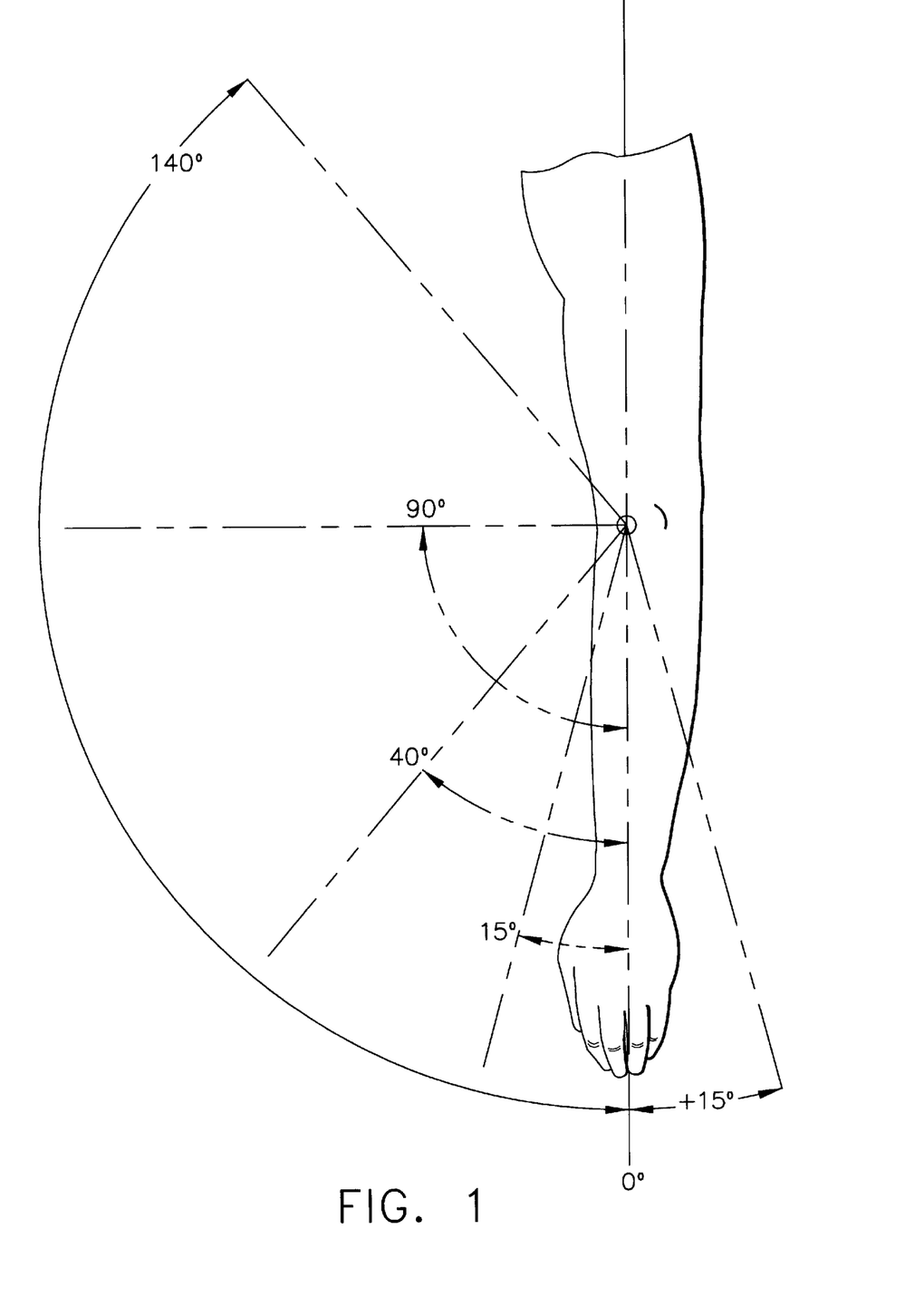
FIG. 1 is a fragmentary side elevational view of a left arm, illustrating the normal range of extension and flexion of the human arm about the elbow joint.

Throughout the drawings, like parts have been given like index numerals. Reference is first made to FIG. 1. As indicated above, the dynamic splint of the present invention will be described in its application to the elbow joint of a human arm. As further indicated above, the dynamic splint may be additionally applicable to any appropriate hinged joint.

FIG. 1 illustrates the normal, full range of motion of the elbow joint. It is generally accepted that the normal range of motion of the elbow joint is from an extended position at 0° to a retracted position at 140° and from the extended position at 0° to a hyper-extended position of +15°.

As indicated above, after a prolonged period in a cast, the flexion muscle group of the arm will be shortened and the extension muscle group will be elongated. As a result, the patient will lose some portion of the overall range of motion. For purposes of an exemplary showing, let it be assumed that the patient can move his arm between about 40° and 140°. However, the flexion muscle group is too short and the extension muscle group is too long to shift the patient's arm from 40° through 0° to +15° in response to signals from the patient's brain. That part of the overall range of motion from 40° to 140° may be designated an active range through which the patient can move his arm. That portion of the overall range of motion from 40° through 0° to +15° may be designated the passive zone through which the patient cannot move his arm.

The primary goal of the dynamic splint of the present invention is to provide a force (in the form of torque) to the elbow joint via the forearm, over a prolonged period of time to influence the synthesis of new tissue and return the contracted flexion muscle group to its proper length. The torque is applied only in the passive zone and not in the active zone. In this way, the dynamic splint does not provide a passive assist to the active muscle movement in the active zone and thus does not interfere with the recovery of the extension muscle group which has become stretched and needs to be partially absorbed.

Figure 2:
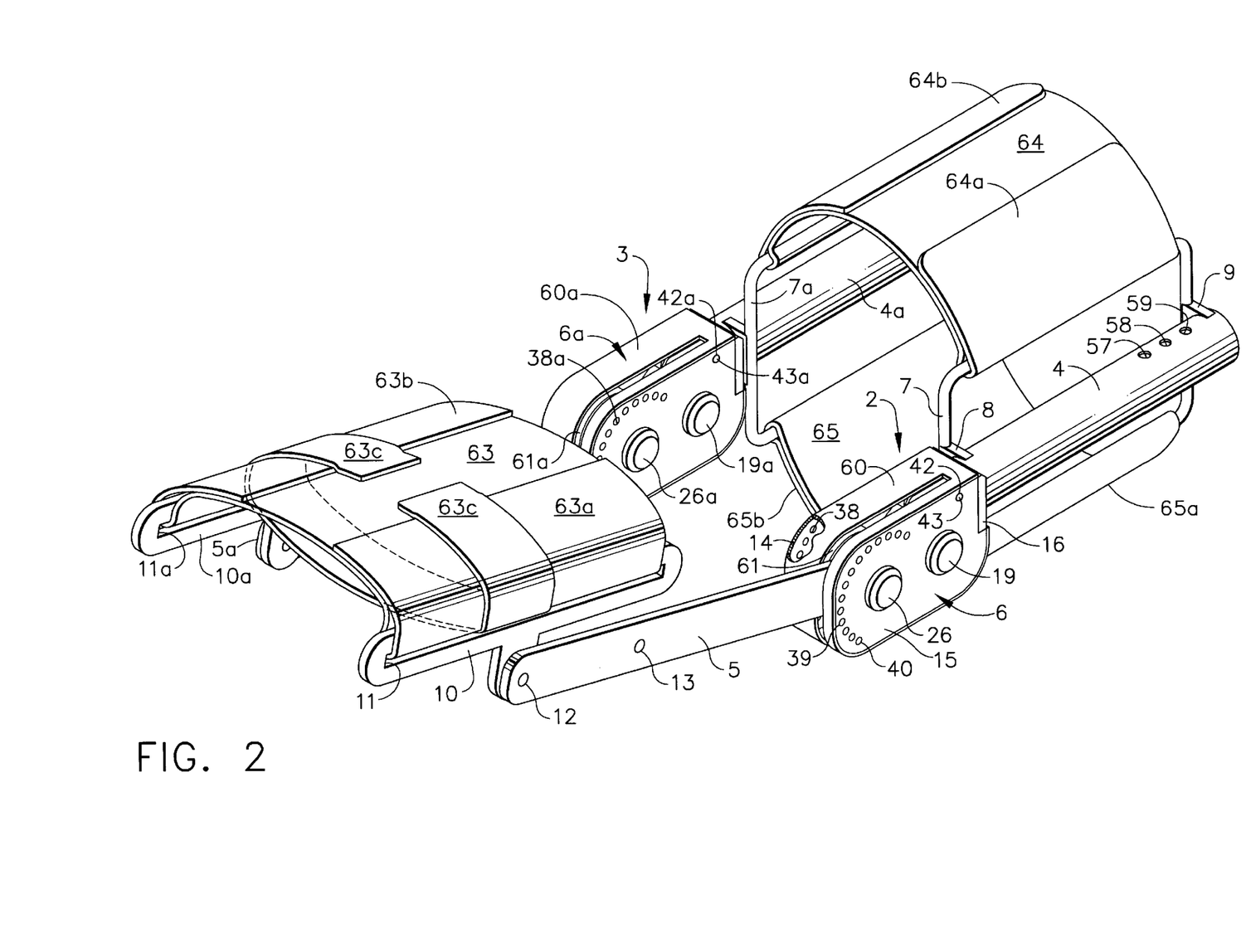
FIG. 2 is a perspective view of a dual member splint of the present invention.

Reference is now made to FIG. 2 wherein the dynamic splint of the present invention is generally indicated at 1. The splint comprises a pair of side frame assemblies, generally indicated at 2 and 3. Side frame assembly 2 is separately illustrated in FIG. 3. Side frame assembly 2 comprises a first tubular strut 4, a second lever-like strut 5 and an intermediate gear housing 6. The first tubular strut 4 is provided with a cuff mounting element such as a rectangular cuff mounting frame 7, made of rod stock and attached to the inwardly facing surface portion of the first tubular strut 4 by brackets 8 and 9.

Figure 3:
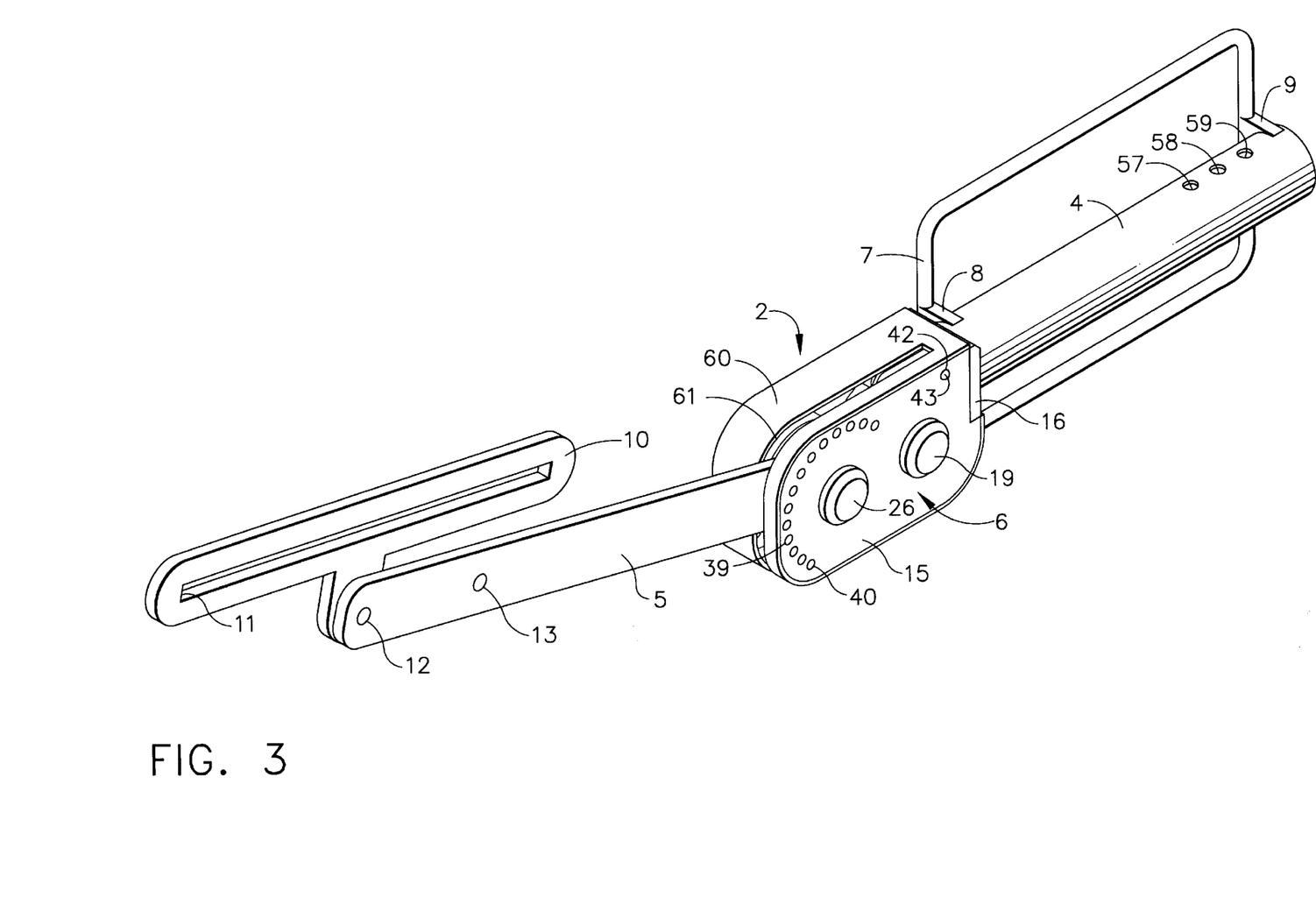
FIG. 3 is a perspective view of the near splint member of FIG. 2.

The second lever-like strut 5 is provided with a T-shaped cuff mounting member 10 having an elongated slot 11 formed therein. The T-shaped cuff mounting member 10 is pivotally affixed to the second strut 5 by means of a bolt or other appropriate pivot device (not shown) passing through coaxial holes in the strut 5 and the cuff mounting member 10. In FIG. 3, the hole in strut 5 is shown at 12, while the hole in the cuff mounting member 10 is obscured by the strut 5. The strut 5 is preferably provided with one or more additional perforations 13 so that the cuff mounting member 10 may be pivotally attached to the strut member 5 at two or more different places. This provides one way to adjust the torque applied by the splint. The further from the gear housing the mounting member 10 is pivoted to the lever-like strut 5, the less the torque. The nearer to the gear housing the mounting member 10 is pivoted to the lever-like strut 5, greater the torque.

Reference is now made to FIGS. 4 and 5 which again illustrate the side frame assembly 2. As is best shown in FIG. 4, the gear housing 6 comprises a pair of side panels 14 and 15 joined together in parallel spaced relationship by a block 16 having a central bore 17 (see FIG. 5).

A first shoulder bolt 19 passes through a clearance hole 20 in side panel 15 and is engaged in a threaded hole 21 in side panel 14. A first gear 22 and a cam wheel 23 are rotatively mounted on shoulder bolt 19. Furthermore, first gear 22 and cam wheel 23 are pinned together as at 24. It will be noted that for a majority of its periphery, the cam wheel 23 is grooved as at 23a. The first gear 22 is provided with 11 teeth, one tooth missing as at 25. The first shoulder bolt 19 also passes through a spacer 19a and a plate 19b with clearance, the purposes of the spacer 19a and plate 19b will be apparent hereinafter.

A second shoulder bolt 26 passes through clearance hole 27 in side panel 15 and is threadedly engaged in a threaded hole 28 in side panel 14. The shoulder bolt 26 pivotally mounts between side panels 14 and 15 a second gear 29 and one end of the lever-like strut 5. The gear 29 is provided with six teeth, while six additional teeth in a row are missing from gear 29, as at 30. The gears 22 and 29 can be cut from identical blanks. The gear 29 is provided with a plurality of evenly spaced holes 31 arranged in a circular array. The second strut 5 is provided with a hole 32. Any one of gear holes 31 can be located coaxially with strut hole 32 to receive a pin 33 through the strut hole 32 and the aligned one of the gear holes 31. The purpose of this will be apparent hereinafter.

Figure 4:
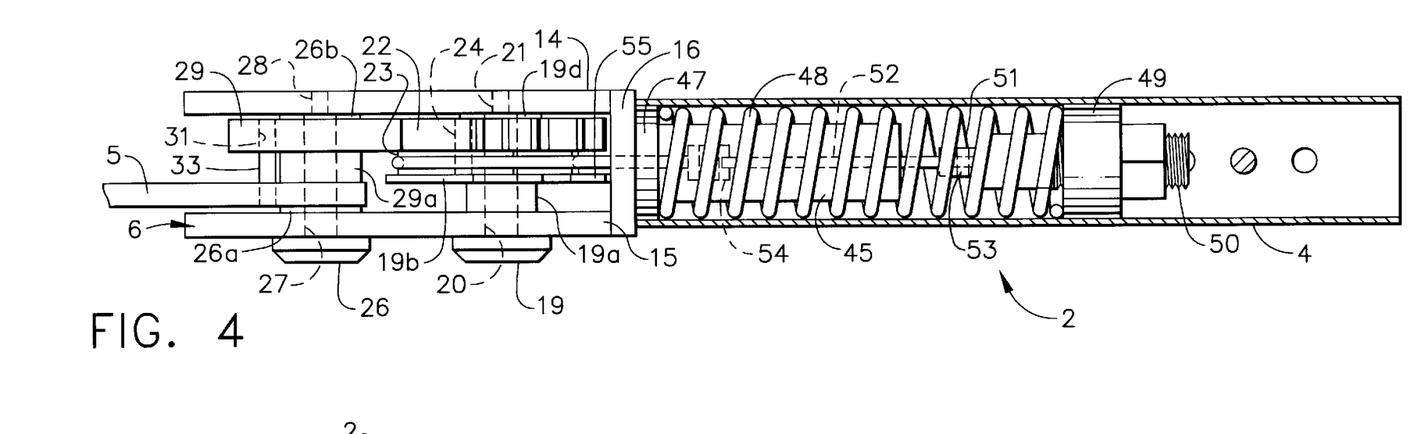
FIG. 4 is a fragmentary plan view of the splint member of FIG. 3, partly in cross-section.
Figure 5:
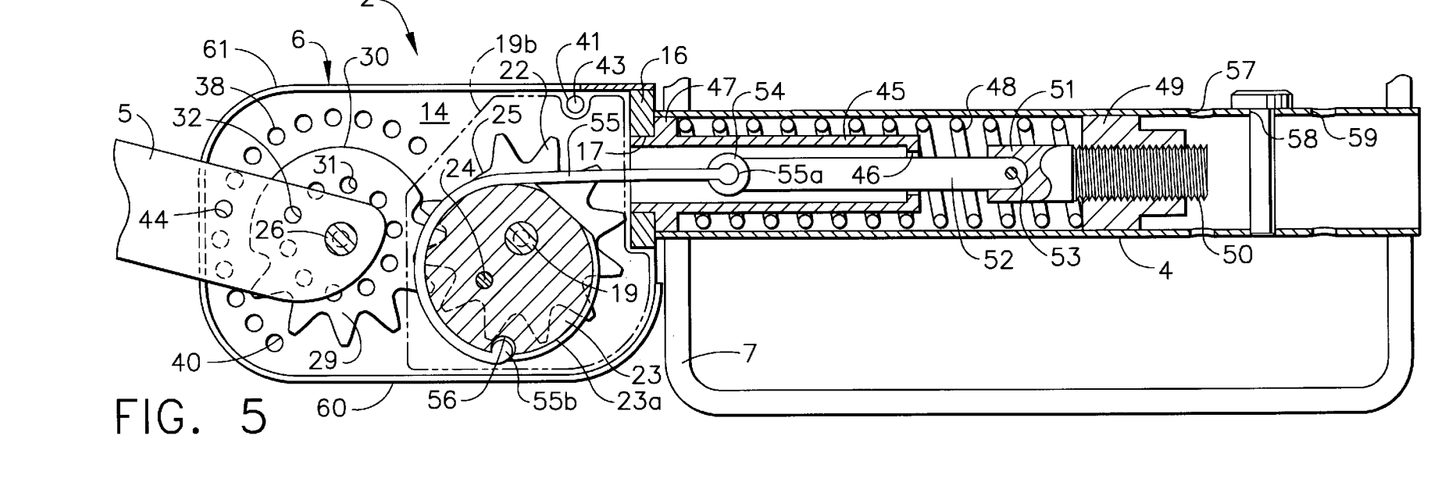
FIG. 5 is a fragmentary, cross-sectional, elevational view of the splint member of FIG. 3.

As is most clearly shown in FIG. 4, the spacer 19a is mounted on shoulder bolt 19 and lies between plate 19b and side panel 15. A spacer 19d is mounted on shoulder bolt 19 and is located between gear 22 and side panel 14. In a similar fashion, the shoulder bolt 26 mounts a spacer 26a located between strut 5 and side panel 15. The shoulder bolt 26 also mounts a spacer 26b located between side panel 14 and the second gear 29.

Figure 7:
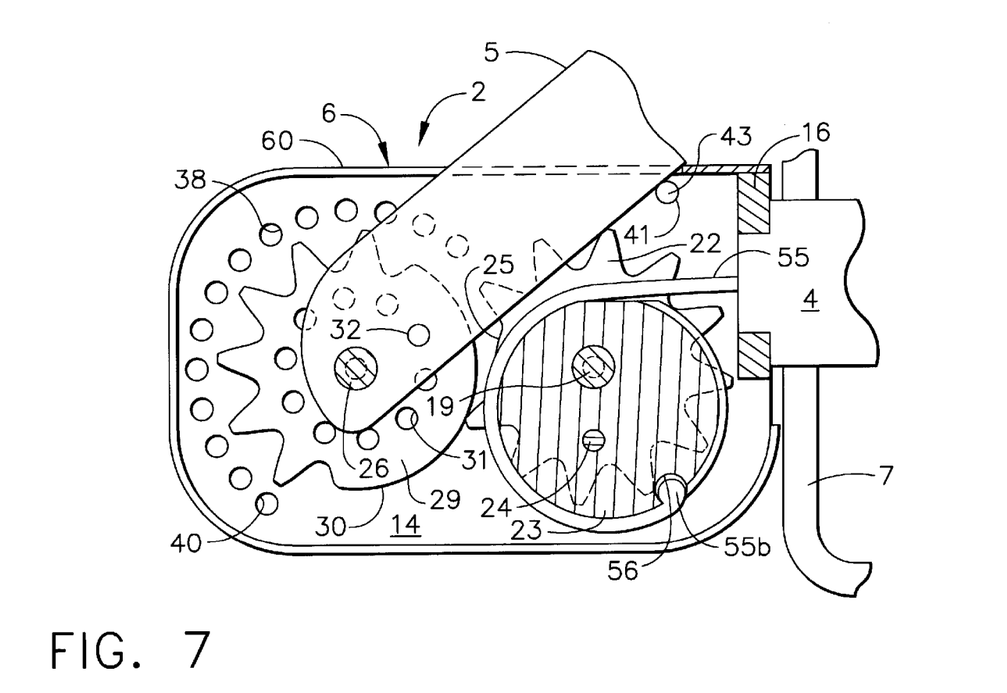
FIG. 7 is a fragmentary cross-sectional view, similar to FIG. 5, but showing the lever-like strut in the 140° position.
Figure 13:
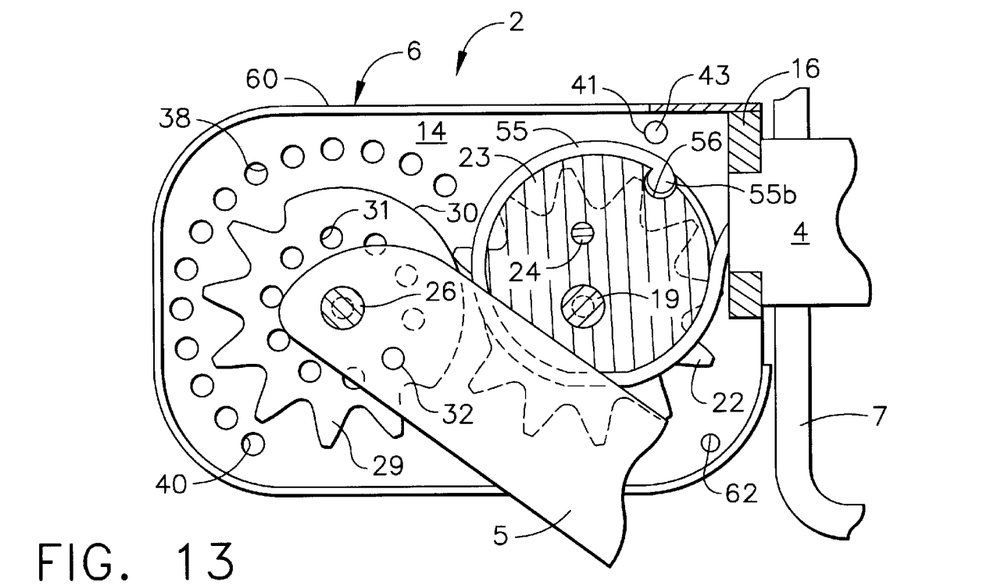
FIG. 13 is a simplified fragmentary cross-sectional view of a gear housing, illustrating the gears and lever-like strut arranged to apply torque in the passive zone to the flexion muscles of a patient's leg.

It will be understood by one skilled in the art that the spacer 19a mounted on pin 19 and the spacer 29a mounted on pin 29 provide clearance for strut 5 when strut 5 is in the position shown in FIG. 7 or in the position shown in FIG. 13.

The plate 19b illustrated in FIGS. 4 and 5 assures that cable 55 will stay within its groove 23a in cam wheel 23.

Both side panels 14 and 15 are each provided with an identical circular array of holes. The holes of the array of side panel 14 are indicated at 38 (see FIG. 5). The holes of the array of side panel 15 are indicated at 39 (see FIG. 2). The holes 38 may be spaced from each other by about 5° to about 10°. The same is true of holes 39. Corresponding ones of holes 38 and 39 are coaxial.

The lowermost ones of the holes 38 and 39 may be provided with a pin 40 which serves as a stop for strut 5 at the +15° point (see FIG. 1). The side panels 14 and 15 of gear housing 6 may also be provided with a coaxial pair of holes 41 and 42 (see FIGS. 3 and 5). A pin 43 is located in perforations 41 and 42 and serves as a stop for strut 5 at the 140° position (see FIG. 1). Thus, the stop pins 40 and 43 are located at the ends of the overall normal range of motion.

It will be noted in FIG. 5 that the strut 5 has a perforation 44 therein which aligns with any one of the coaxial pairs of perforations 38–39. The purpose of this will be apparent hereinafter. The perforations 38 and 39 are referred to as range of motion perforations. Through the use of rollpins or the like, these arrays of holes can be used to limit the range of motion of strut 5 to a range less than from +15° to 140°, as will be further explained hereinafter.

A cylindrical member 45 is located within the tubular strut 4. The forward end of cylindrical member 45 is open and is affixed in the bore 17 of block 16. The rearward end of cylindrical member 45 is closed and is provided with a thin rectangular slot 46. Near its forward end, the cylindrical member 45 has an annular flange 47. The flange 47 serves as a forward seat for a compression spring 48. The remainder of the cylindrical member serves as a guide for compression spring 48. The rearward seat of the compression spring is adjustable and comprises a nut 49 slidably mounted in tubular strut 4. Threadedly engaged in nut 49 there is a bolt 50 having a bifurcated head 51 adapted to receive one end of a thin, flat link 52. The end of the flat link 52 is pinned between the bifurcations by pivot pin 53. It will be noted that link 52 passes with clearance through slot 46 in cylindrical member 45 (see FIG. 5). The forward end of the link 52 ends in a socket 54 in which the enlarged first end 55a of a cable 55 is received. The other enlarged end 55b of cable 55 is mounted in a socket 56 formed in the periphery of cam wheel 23. The nut 49 has an extension engageable by an appropriate socket tool to adjust the position of nut 49 with respect to bolt 50, for reasons to be discussed hereinafter. It will be understood that the flat link 52 in slot 46 will preclude rotation of bolt 50, during rotation of nut 49.

The tubular strut 4 is provided with a plurality of holes in its upper periphery (see FIGS. 3 and 5). For purposes of an exemplary showing, three holes 57, 58 and 59 are shown. Additional holes could be provided, if desired. These holes pass diametrically through the tubular strut 4. All three holes 57, 58 and 59 can serve as visual ports to show the position of nut 49. The through holes 57, 58 and 59 can serve the additional purpose of receiving a headed locking pin (see FIG. 5) to reduce the expansion capabilities of compression spring 48 for reasons to be given hereinafter. The tubular strut of side frame assembly 3 is provided with similar holes for the same purpose.

Reference is now made to FIG. 3. It will be noted in FIG. 3 that the space between the side panels of gear housing 6 can be substantially closed by a specially formed resilient member 60 which may be made of plastic or metal and which may engage the side plates of gear housing 6 with a snap fit (see also FIG. 5). The member 60 is provided with a slot 61 to accommodate movement of the second strut 5. It is within the scope of the invention to mold gear housing 6 as a single, integral one-piece plastic member. Furthermore the side frame assembly 2 may be entirely made of metal, plastic, or a combination thereof.

Reference is now made to FIG. 2. With two exceptions, the side frame assembly 3 may be identical to side frame assembly 2. One exception is the fact that the cuff mounting member 7a is mounted on the opposite side of tubular strut 4a. The second exception is the fact that mounting member 10a is mounted on the opposite side of strut 5a. It would be within the scope of the invention to make the side frame assemblies 2 and 3 total mirror images of each other, if desired.

Since side frame assembly 3 is, with the noted exceptions, identical to side frame assembly 2, like parts have been given like index numerals followed by "a". It will be noted from FIG. 2 that the cuff mounting members 10 and 10a, mounted at the ends of lever-like struts 5 and 5a support a cuff member 63. The ends 63a and 63b of cuff member 63 pass through slots 11 and 11a, respectively of cuff mounting members 10 and 10a and overlap the cuff member 63 in the manner shown. They may be releasably held in the positions shown in FIG. 2 by any appropriate means such as hook and loop tape strips, snaps, hook and eye elements, or the like. It will be noted that the cuff member 63 forms an inverted hammock-like cuff member and is shown positioned to apply constant torque to the patient's forearm to increase the length of the patient's flexion muscle group. In an instance where it is necessary to increase the length of a patient's extension muscle group, the cuff member 63 will be inverted by simply rotating the cuff mounting members 10 and 10a about 180°.

As shown in FIG. 2, a relatively narrow strap 63c is releasably attached at its ends (by hook and loop tape or the like, not shown) to cuff ends 63a and 63b, passing through slots 11 and 11a. The purpose of this strap is to keep cuff 63 associated with the patient's forearm at all times.

The rectangular cuff mounting members 7 and 7a, attached respectively to tubular struts 4 and 4a mount upper and lower cuff members 64 and 65 to make a cylindrical, 360° cuff assembly. The ends 64a and 64b of cuff member 64 pass about the longitudinal upper portions of cuff mounting members 7 and 7a and overlap the cuff member 64 in substantially the same way described with cuff member 63 and may be held in position in any one of the ways described with respect to cuff member 63. Similarly, the ends 65a and 65b of cuff member 65 pass about the longitudinal lower portions of cuff mounting members 7 and 7a and overlap and are releasably attached to the cuff member 65 in the same manner described with respect to cuff member 63. It would be within the scope of the present invention to provide the struts 5 and 5a with a cylindrical cuff assembly similar to cuff members 64 and 65.

If the dynamic splint of the present invention is to be mounted on a limb to be rehabilitated it will be affixed thereto by the above-described cuff members and the side frame assemblies 2 and 3 will lie to either side of the joint in question. Therefore, depending upon the limb and joint being treated, the dynamic splint of the present invention may be made in a number of sizes, or it may be made adjustable to provide a size range.

Figure 6:
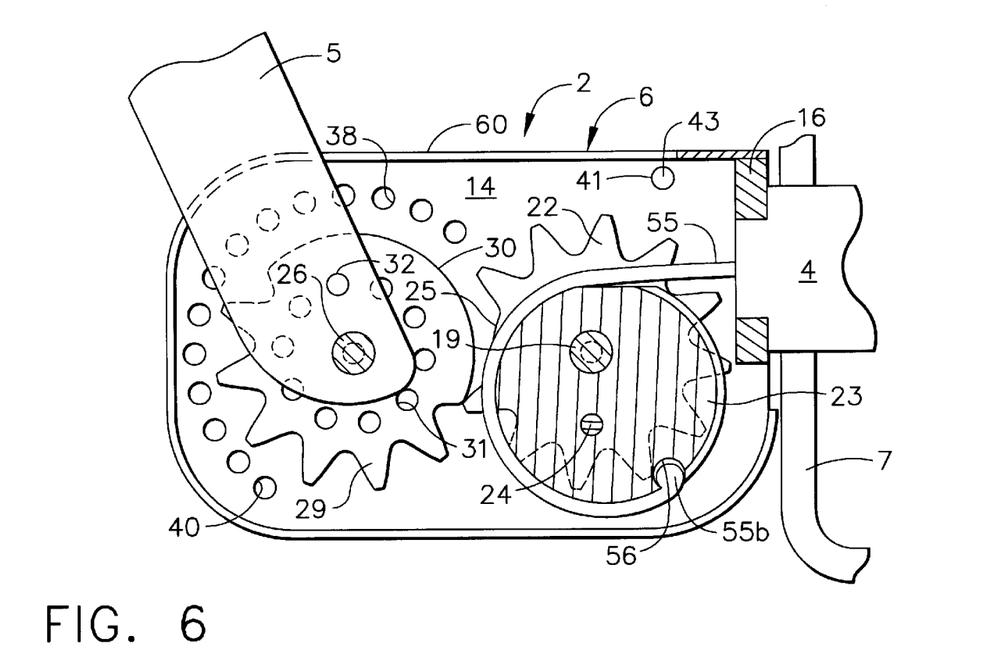
FIG. 6 is a fragmentary cross-section view, similar to FIG. 5, and illustrating the position of the gears at the point of transition between the passive range and the active range.

It will be remembered that in the exemplary embodiment, it was assumed that the patient cannot or has difficulty moving his forearm between about 40° and +15° of the normal range of movement. Therefore, the constant torque applied to the second struts 5 and 5a must begin when the forearm enters the passive range at about 40°. Similarly, the torque applied to the second struts should cease when the forearm enters the active range at about the 40° juncture between the active range and the passive range. To accomplish this, the strut 5 must be pinned through its hole 32 and the appropriate one of the holes 31 of gear 29 so that the relationship between the strut 5 and the gear 29 in such that the gear 29 will begin to mesh with gear 22 at a point just above the 40° mark as shown in FIG. 6 and will be fully interengaged when the strut 5 enters the passive zone as shown in FIG. 5. In addition, the nut 49 should be adjusted to assure that when the gears 29 and 22 are interengaged, the spring 48, cable 55, cam wheel 23 and gear 22 will apply the desired amount of constant torque to the gear 29 and strut 5. The same adjustments are made with respect to the side frame assembly 3. At this point, the dynamic splint 1 is ready to be applied to the patient's arm. Cuff elements 64 and 65 are firmly but comfortably closed about the patient's upper arm in such a way that the axes of shoulder bolts 26 and 26a are substantially coaxial with the bending axis of the elbow joint. The cuff member 63 is located atop the forearm, with the strap 63c therebelow.

Figure 8:
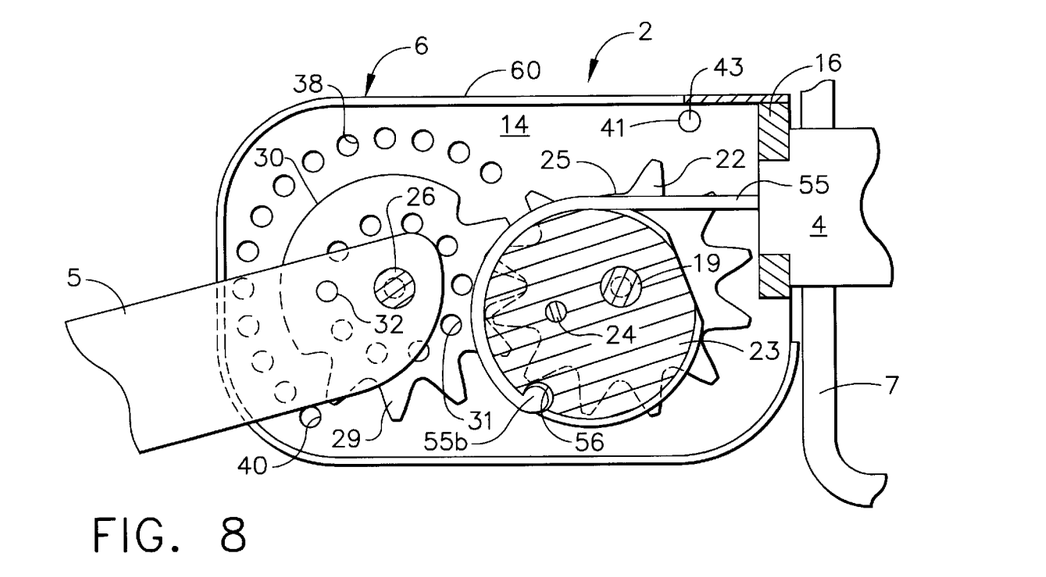
FIG. 8 is a fragmentary cross-sectional view similar to FIG. 5, but showing the lever-like strut at +15°.

FIG. 6 illustrates the parts in their positions as the patient's arm enters the passive zone of 40°to +15°. Thus gears 22 and 29 are just about to mesh so that spring 48, cable 55, cam wheel 23 and gear 22 can apply a torque to gear 29 and strut 5. As the patient moves his arm toward the passive zone, strut 5 and gear 21 will turn counterclockwise. When gears 22 and 29 mesh, the assembly of spring 48, cable 55, cam wheel 23 and gear 22 is free to apply the torque to gear 29 and lever 5, causing them to be urged in a counterclockwise direction, gear 22 and cam wheel 23 being rotated in a clockwise direction by cable 55 and spring 48. FIG. 6 can also be considered to show an instance where the patient is lifting his forearm, toward his shoulder and is entering the active zone. Under these circumstances the gears 22 and 29 are just beginning to disengage. Gears 29 and strut 5 are being rotated in a clockwise direction by the patient's arm. When one or both of the teeth of gear 22 adjacent space 25 contact the toothless peripheral part of gear 29, gear 22 and cam wheel 23 are precluded from rotation and apply no torque force to gear 29 and strut 5. FIG. 7 shows the positions of the parts at the 140° portion of the overall range of motion, with gears 22 and 29 disengaged. FIG. 8 illustrates the positions of the parts at the +15° end of the range of motion, determined by pin 40. Since +15° is in the passive zone, gears 22 and 29 are meshed and a low grade torque force is applied to gear 29 and strut 5.

Other adjustments can be made in the side frame assemblies. For example, as indicated above, pins can be located in appropriate coaxial pairs of the range-of-motion holes 38 and 39 (see FIGS. 3 and 5) to adjust the overall range-of-motion to something less than the normal range-of-motion determined by pin 40 and pin 43 (see FIG. 5). For example, the extent of the passive range can be changed or reduced in orthopedic and neurological cases to minimize spasticity and/or tissue trauma.

A roll pin or the like may be caused to pass through the hole 32 of strut 5 and the similar hole of strut 5a and through identical selected pairs of range-of-motion adjustment holes 38 and 39 of gear housing 6 and the identical pair of range-of-motion adjustment holes 38a and 39a in gear housing 6a to lock the struts 5 and 5a in the same position and render the splint an immobilization splint.

As indicated above, the holes 57, 58 and 59 of strut 4 may be used as sight holes for low, standard and high spring adjustment. The same is, of course, true of the similar holes formed in strut 4a. A pin may be inserted in any one of holes 57, 58 and 59 through strut 4, and the corresponding through hole of strut 4a, to limit the amount of expansion of their respect springs to limit the torque which will be applied to struts 5 and 5a. A hole similar to holes 57–59 may be provided in each of struts 4 and 4a, which holes are so located that, when provided with a pin, their respective springs will be locked to prevent any torque from being applied to struts 5 and 5a.

In some instances, due to a stroke, a neurological problem, disease, burns, or the like, it is necessary to maintain an arm in an extended position for a long period of time. The extension group of muscles will become contracted, and the flexion muscle group will become stretched and may grow longer. When this occurs, the normal active range of movement can become greatly diminished.

Figure 9:
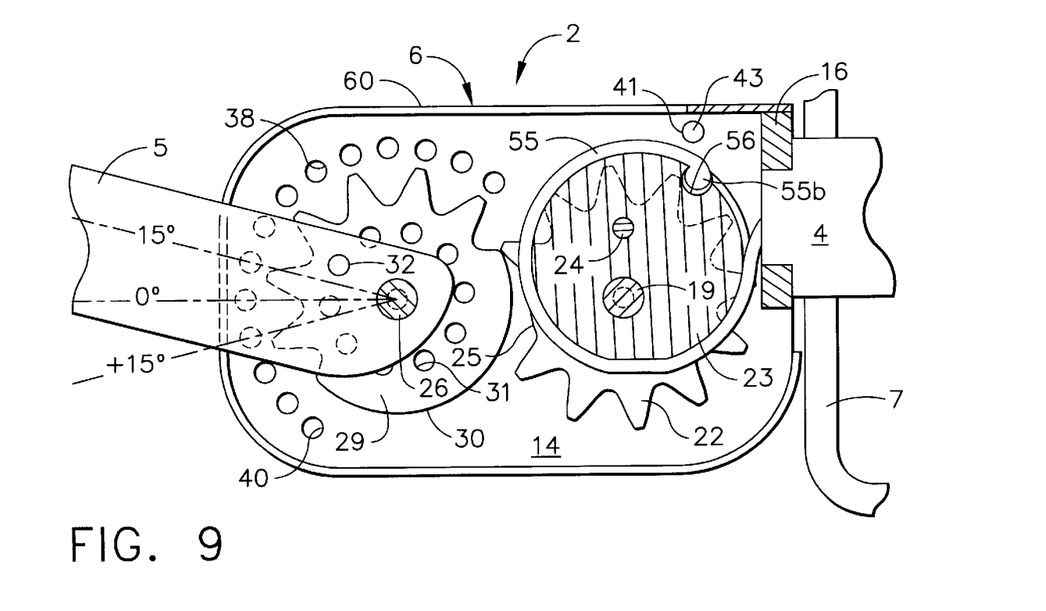
FIG. 9 is a fragmentary cross-sectional view showing the cam and gear reversed for the application of low level torque to shortened or contracted muscles of the extension group.

For purposes of an exemplary explanation, let it be assumed that the patient's arm, having been held in an extended position for a long period of time, has an active range from +15° to 15°, and is unable to bend at the elbow to bring the forearm from about 15° to about 140°. Thus +15° to 15° is the active zone, and 15° to 140° is the passive zone. The splint of the present invention may be used to apply a constant torque to the forearm throughout this passive zone. This is accomplished by modifying the splint in the manner illustrated in FIG. 9. In this instance, the first gear 22 and cam wheel 23 are separated by removal of pin 24 and are thereafter turned upside down. The gear 22 and the cam wheel 23 are arranged to assume the positions shown in FIG. 9. It will be noted that gear 22 is again adjacent gear housing wall 14. Gear 22 and cam wheel 23 are reattached by pin 24. As a consequence, the cable 55 and the spring 48 will urge cam wheel 23 and the first gear 22 (to which cam wheel 23 is attached) to rotate in a counter-clockwise direction. Meanwhile, the second gear 29 is positioned as shown in FIG. 9 and the lever-like strut 5 is connected to the second gear 29 by a pin passing through an appropriate one of the holes 31 in the gear and the hole 32 in the strut 5. It will be noted that strut 5 is lying at an angle of about 15° which constitutes the junction of the active and passive zones.

It will be apparent from FIG. 9 that the first gear 22 and second gear 29 are at a position where their teeth are beginning to mesh, with the first gear 22 and cam wheel 23 turning in a counterclockwise direction, this will cause the second gear 29 to turn in a clockwise direction. It will be apparent that FIG. 9 may also be considered as illustrating the gears 22 and 29 in a position wherein they are about to become disengaged. If the patient moves his arm from 15° to 0° or +15°, the second gear 29 will move in a counter-clockwise direction along with the lever-like strut 5 causing the first gear 22 to rotate in a clockwise direction. This will immediately bring the toothless portion 30 of the second gear 29 opposite the missing tooth portion 25 of first gear 22. As a consequence of this, the first gear 22 will be precluded from rotating and will have no influence upon the second gear 29 throughout the active zone of from +15° to 15°. Throughout the passive zone, the spring 48, cable 55, cam wheel 23 and first gear 22 will cause a torque force to be applied to the lever-like strut 5 tending to lift the forearm and applying pressure thereto to aid the extension muscle group to stretch and grow. It will be understood that the very same modifications will be made to the side frame assembly 3.

Figure 10:
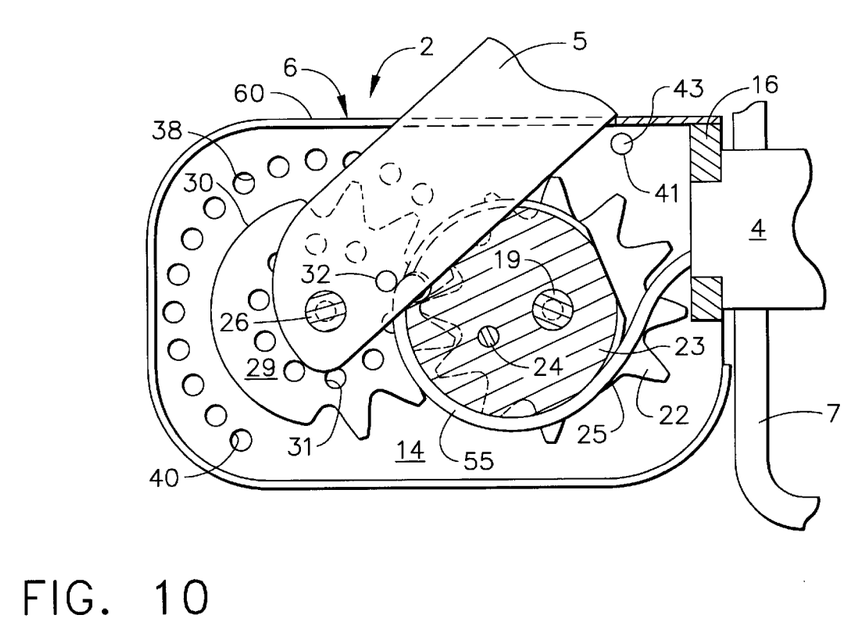
FIG. 10 illustrates the structure of FIG. 9 with the lever-like strut at 140°.
Figure 11:
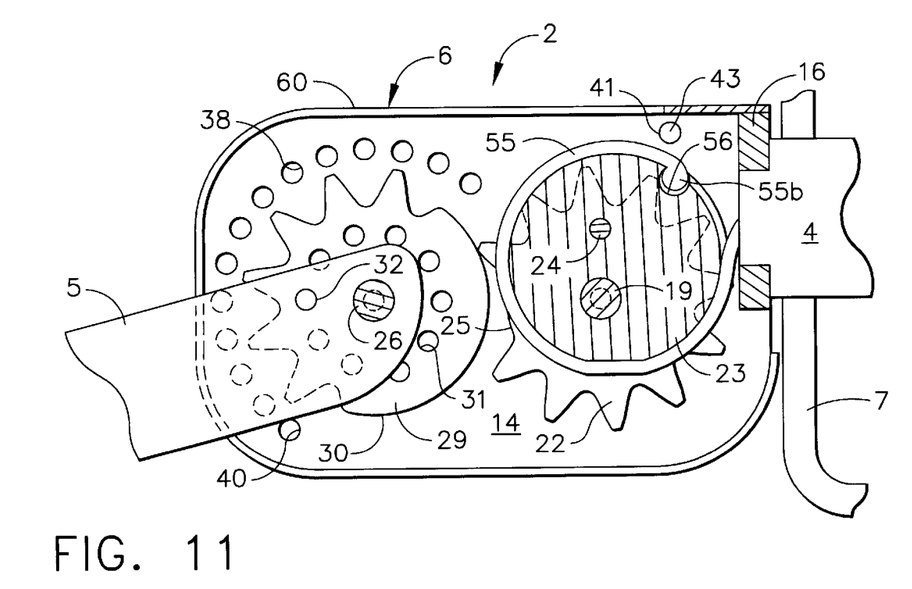
FIG. 11 illustrates the structure of FIG. 9 with the lever-like strut at +15°.

FIG. 10 is a fragmentary, semi-diagrammatic view similar to FIG. 9, and shows the second lever-like strut 5 approaching the 140° position. FIG. 11 is similar to FIG. 10, but shows the lever-like strut 5 at the +15° position. It will be obvious that torque will be applied to the second gear 29 and the strut 5 from about 15° to about 140°, while from about 15° to +15° no torque will be applied to gear 29 and lever 5.

Figure 12:
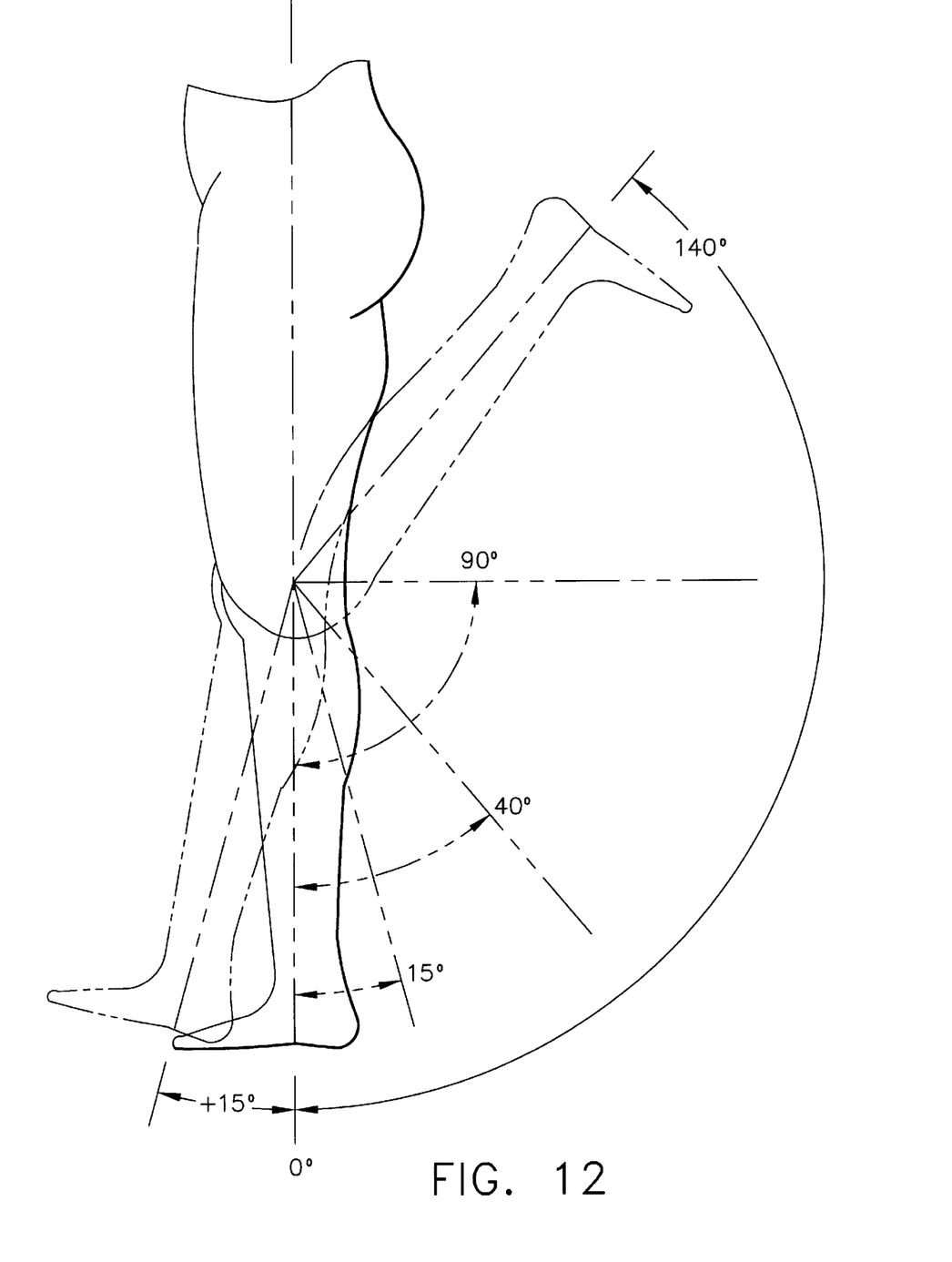
FIG. 12 is a fragmentary side elevational view of a left leg illustrating the normal range of extension and flexion of the human leg about the knee joint.

Reference is now made to FIG. 12. FIG. 12 illustrates the normal, full range of motion of a knee joint. It is generally accepted that the normal full range of motion is from 0° to 140° and from 0° to a hyper-extended position of +15°. It will be noted, however, that the knee joint bends in a manner opposite to that of the elbow.

As in the case of the elbow described above, if the leg is in a cast for a prolonged period, the flexion muscle group of the leg will be shortened and the extension muscle group will be elongated. This causes the patient to lose some portion of the overall range of motion. Let us assume, for purposes of illustration, that the patient is capable of moving his leg from about 40° to about 140°. However, he cannot move his leg from about 40° to about +15°.

Reference is now made to FIG. 13 wherein one splint side frame assembly 2 is illustrated and shows the lever-like strut 5 at about 140°. The first gear 22 and the cam wheel 23 are in the condition shown and described with respect to FIG. 9. It will be noted that first gear 22 and second gear 29 are not meshed. First gear 22 is being urged in a counter-clockwise direction, but is precluded from rotation by engagement with the toothless part of second gear 29. This lack of meshing occurs between about 40° and about 140° and the patient is free to swing his leg through this active range without applied torque from the first gear 22. Clockwise movement of second gear 29 and lever-like strut 5 into the passive zone at about 40° will cause gear 22 to mesh with gear 29, gear 22 applying torque to gear 29 throughout the passive range. A stop pin may be inserted in an appropriate pair of holes 38–39 to serve as a stop at the +15° mark. A pair of holes (one of which is shown at 62 in FIGS. 13 and 14) may be provided for a stop pin defining the 140° position of strut 5. Also, the pin 40 will be relocated in an appropriate pair of holes 38–39 to mark the +15° end of the normal range. It would be within the scope of the invention to add additional holes 38–39 to the gear housing.

The arrangement of FIG. 13 is set up to treat the flexion muscle group, to stretch the flexion muscle group to enable the patient to attain a full range of motion about his knee joint. In some instances, however, the extension muscle group is shortened and must be stretched. This can be accomplished by the arrangement illustrated in FIG. 14.

Figure 14:
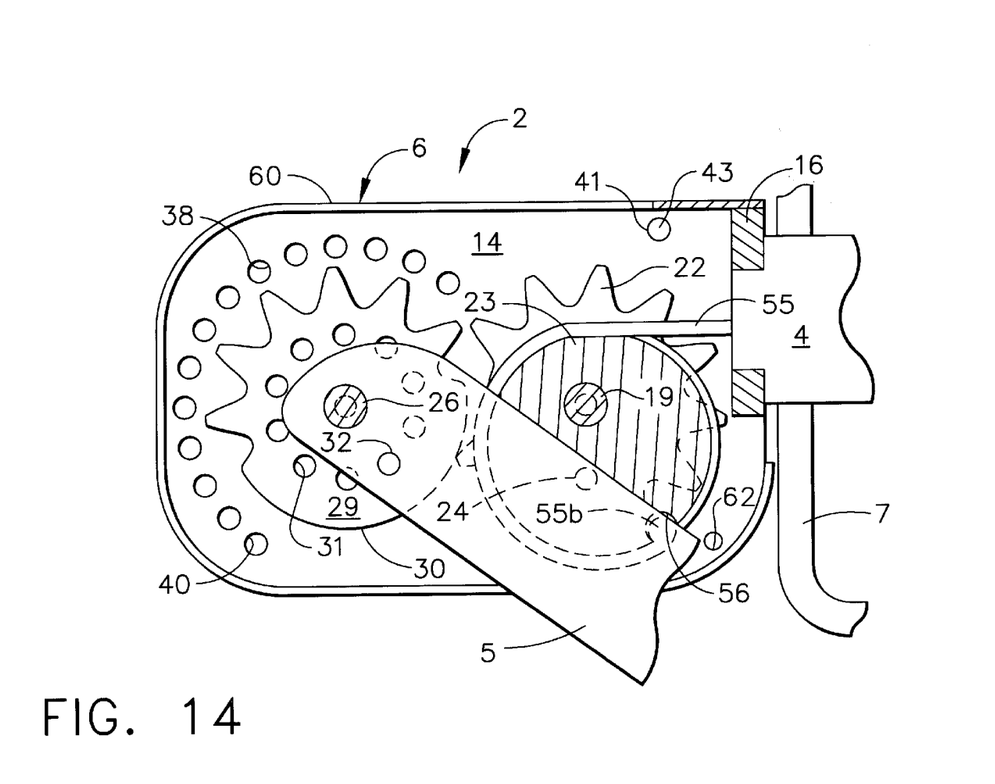
FIG. 14 is a simplified fragmentary cross-sectional view of a gear housing, illustrating the gears and lever-like strut arranged to apply torque in the passive zone to the extension muscles of a patient's leg.

For purposes of an exemplary illustration, let it be assumed that the patient is capable of moving his leg from +15° to 40°, but the extension muscle group is too short to enable him to reach 140° (see FIG. 12). FIG. 14 illustrates an arrangement of the gears 22 and 29, as well as strut 5 such that the gears begin to mesh at about 40°. The range from +15° to 40° is the active range and no torque is applied by gear 22. Once the 40° position has been reached, the gears will begin to mesh and gear 22 will apply to gear 29 and strut 5a torque urging gear 29 and strut 5 in a counter-clockwise direction.

From the above description, it will be seen that the splint of the present invention is very versatile in its application and under any circumstance can be adjusted to apply a preadjusted torque force only within the passive zone. While most applications will have two side frames 2 and 3 adjusted to operate together in the same manner, it is within the scope of the invention to use just one side frame in certain applications. This, of course, would modify the nature of the cuffs used.

Modifications may be made in the invention without departing from the spirit of it.

What is claimed:

1. A dynamic splint for applying a constant pre-adjusted torque across a hinged joint of a patient, the joint having a normal full range of motion divided into an active portion through which the patient can pivot the joint and a passive portion through which the patient cannot pivot the joint due to connective tissue contracture, said dynamic splint comprising a pair of spaced-apart side frame assemblies, said side frame assemblies each having a first strut; a gear housing mounted on one end of said first strut; a first gear rotatably mounted in said gear housing adjacent to said first strut, said first gear having a plurality of teeth and a first missing teeth portion of said first gear wherein at least one of said teeth is missing; a second gear rotatably mounted in said gear housing adjacent to said first gear, said second gear having a plurality of teeth and a second missing teeth portion of said second gear having a plurality of adjacent teeth missing, wherein said teeth of said first gear and said teeth of said second gear mesh when said first gear and said second gear are rotated in said gear housing to position said teeth of said first gear adjacent to said teeth of said second gear and said teeth of said first gear disengage from said teeth of said second gear when said first gear and said second gear are rotated in said gear housing to position said first missing teeth portion of said first gear adjacent to said second missing teeth portion of said second gear; a second strut having one end pivotally mounted in said gear housing and pivotable through the full range of motion of the joint, said second strut releasably attached to said second gear at a selected one of a plurality of positions on said second gear, said selected one of a plurality of positions corresponding to the transition point between the active and passive portions of the full range of motion of the joint, wherein said teeth of said first gear and said teeth of said second gear mesh as said second strut is pivoted through the passive portion of the full range of motion of the joint and said teeth of said first gear and said teeth of said second gear are disengaged as said second strut is pivoted through the active portion of the full range of motion of the joint; bias means operably connected to said first gear for exerting a pre-adjusted torque on said first gear, whereby the pre-adjusted torque is constantly applied to said second strut through the passive portion of the full range of movement of the joint and no torque is applied to said second strut through the active portion of the full range of movement of the joint; and a first cuff assembly supported by said first struts of said side frame assemblies and a second cuff assembly supported by said second struts of said side frame assemblies.

2. The dynamic splint of claim 1 comprising a pair of cuff mounting frames provided in facing relationship on said first struts, respectively, and wherein said first cuff assembly is mounted between said pair of cuff mounting frames.

3. The dynamic splint of claim 1 comprising a pair of cuff mounting members provided in facing relationship on said second struts, respectively, and wherein said second cuff assembly is mounted between said pair of cuff mounting members.

4. The dynamic splint of claim 1 comprising a pair of cuff mounting frames provided in facing relationship on said first struts, respectively, and wherein said first cuff assembly is mounted between said pair of cuff mounting frames; and comprising a pair of cuff mounting members provided in facing relationship on said second struts, respectively, and wherein said second cuff assembly is mounted between said pair of cuff mounting members.

5. The dynamic splint of claim 1 comprising a plurality of aligned range of motion perforations provided in said housing about the periphery of said second gear and a pin for extension through a selected pair of said range of motion perforations for stopping said second strut at a selected point in the full range of motion of the joint.

6. The dynamic splint of claim 5 comprising a pair of cuff mounting frames provided in facing relationship on said first struts, respectively, and wherein said first cuff assembly is mounted between said pair of cuff mounting frames.

7. The dynamic splint of claim 5 comprising a pair of cuff mounting members provided in facing relationship on said second struts, respectively, and wherein said second cuff assembly is mounted between said pair of cuff mounting members.

8. The dynamic splint of claim 5 comprising a pair of cuff mounting frames provided in facing relationship on said first struts, respectively, and wherein said first cuff assembly is mounted between said pair of cuff mounting frames; and comprising a pair of cuff mounting members provided in facing relationship on said second struts, respectively, and wherein said second cuff assembly is mounted between said pair of cuff mounting members.

9. The dynamic splint of claim 5 comprising a strut perforation provided in said second strut and wherein said pin can be extended through a selected pair of said range of motion perforations and said strut perforation for locking said second strut at a selected point in the full range of motion of the joint.

10. The dynamic splint of claim 9 comprising a pair of cuff mounting frames provided in facing relationship on said first struts, respectively, and wherein said first cuff assembly is mounted between said pair of cuff mounting frames.

11. The dynamic splint of claim 9 comprising a pair of cuff mounting members provided in facing relationship on said second struts, respectively, and wherein said second cuff assembly is mounted between said pair of cuff mounting members.

12. The dynamic splint of claim 9 comprising a pair of cuff mounting frames provided in facing relationship on said first struts, respectively, and wherein said first cuff assembly is mounted between said pair of cuff mounting frames; and comprising a pair of cuff mounting members provided in facing relationship on said second struts, respectively, and wherein said second cuff assembly is mounted between said pair of cuff mounting members.

13. A dynamic splint for applying a constant pre-adjusted torque across a hinged joint of a patient, the hinged joint having a normal full range of motion divided into an active portion through which the patient can pivot the joint and a passive portion through which the patient cannot pivot the joint due to connective tissue contracture, said dynamic splint comprising a pair of substantially parallel side frame assemblies, said side frame assemblies each having a tubular first strut; a gear housing mounted on one end of said first strut; a first gear rotatably mounted in said gear housing adjacent to said first strut, said first gear having a plurality of teeth and a first missing teeth portion of said first gear wherein at least one of said teeth is missing; a second gear rotatably mounted in said gear housing adjacent to said first gear, said second gear having a plurality of teeth and a second missing teeth portion of said second gear having a plurality of adjacent teeth missing, wherein said teeth of said first gear and said teeth of said second gear mesh when said first gear and said second gear are rotated in said gear housing to position said teeth of said first gear adjacent to said teeth of said second gear and said teeth of said first gear disengage said teeth of said second gear when said first gear and said second gear are rotated in said gear housing to position said first missing teeth portion of said first gear adjacent to said second missing teeth portion of said second gear; a second strut having one end pivotally mounted in said gear housing and pivotable through the full range of motion of the joint, said second strut releasably attached to said second gear at a selected one of a plurality of positions corresponding to the transition point between the active and passive portions of the full range of motion of the joint, wherein said teeth of said first gear and said teeth of said second gear mesh as said second strut is pivoted through the passive portion of the full range of motion of the joint and said teeth of said first gear and said teeth of said second gear are disengaged as said second strut is pivoted through the active portion of the full range of motion of the joint; a cam wheel rotatably mounted with said first gear, a cable attached at one end to said cam wheel and an adjustable compression spring mounted in said first strut and attached to the other end of said cable for exerting a pre-adjusted torque on said first gear, whereby the pre-adjusted torque is constantly applied to said second strut throughout the passive portion of the full range of movement of the joint and no torque is applied to said second strut throughout the active portion of the full range of movement of the joint; and a first cuff assembly supported by said first strut of said side frame assemblies and a second cuff assembly supported by said second struts of said side frame assemblies.

14. The dynamic splint of claim 13 comprising a pair of cuff mounting frames provided in facing relationship on said first struts, respectively, and wherein said first cuff assembly is mounted between said pair of cuff mounting frames.

15. The dynamic splint of claim 13 comprising a pair of cuff mounting members provided in facing relationship on said second struts, respectively, and wherein said second cuff assembly is mounted between said pair of cuff mounting members.

16. The dynamic splint of claim 13 comprising a pair of cuff mounting frames provided in facing relationship on said first struts, respectively, and wherein said first cuff assembly is mounted between said pair of cuff mounting frames; and comprising a pair of cuff mounting members provided in facing relationship on said second struts, respectively, and wherein said second cuff assembly is mounted between said pair of cuff mounting members.

17. The dynamic splint of claim 13 comprising a plurality of aligned range of motion perforations provided in said housing about the periphery of said second gear and a pin for extension through a selected pair of said range of motion perforations and stopping said second strut at a selected point in the full range of motion of the joint.

18. The dynamic splint of claim 17 comprising a strut perforation provided in said second strut and wherein said pin can be extended through a selected pair of said range of motion perforations and said strut perforation for locking said second strut at a selected point in the full range of motion of the joint.

19. The dynamic splint of claim 18 comprising a pair of cuff mounting frames provided in facing relationship on said first struts, respectively, and wherein said first cuff assembly is mounted between said pair of cuff mounting frames; and comprising a pair of cuff mounting members provided in facing relationship on said second struts, respectively, and wherein said second cuff assembly is mounted between said second pair of cuff mounting members.

20. A dynamic splint for applying a constant pre-adjusted torque across a hinged joint of a patient, the joint having a normal full range of motion divided into an active portion through which the patient can pivot the joint and a passive portion through which the patient cannot pivot the joint due to connective tissue contracture, said dynamic splint comprising a pair of spaced-apart, substantially parallel side frame assemblies, said side frame assemblies each having a tubular first strut; a gear housing mounted on one end of said first strut; a first gear rotatably mounted in said gear housing adjacent to said first strut, said first gear having a plurality of teeth and a first missing teeth portion of said first gear wherein at least one of said teeth is missing; a second gear rotatably mounted in said gear housing adjacent to said first gear, said second gear having a plurality of teeth and a second missing teeth portion of said second gear having a plurality of adjacent teeth missing, wherein said teeth of said first gear and said teeth of said second gear mesh when said first gear and said second gear are rotated in said gear housing to position said teeth of said first gear adjacent to said teeth of said second gear and said teeth of said first gear disengage said teeth of said second gear when said first gear and said second gear are rotated in said gear housing to position said first missing teeth portion of said first gear adjacent to said second missing teeth portion of said second gear; a second strut having one end pivotally mounted in said gear housing and pivotable through the full range of motion of the joint, said second strut releasably attached to said second gear at a selected one of a plurality of positions corresponding to the transition point between the active and passive portions of the joint, wherein said teeth of said first gear and said teeth of said second gear mesh as said second strut is pivoted through the passive portion of the full range of motion of the joint and said teeth of said first gear and said teeth of said second gear are disengaged as said second strut is pivoted through the active portion of the full range of motion of the joint; a cam wheel rotatably mounted with said first gear, a cable attached at one end to said cam wheel an adjustable compression spring mounted in said first strut, a threaded compression nut provided in said first strut for compressing said compression spring against said housing and a threaded bolt attached to the other end of said cable and threaded through said compression nut for exerting a pre-adjusted torque on said first gear, whereby the pre-adjusted torque is constantly applied to said second strut through the passive portion of the full range of motion of the joint and no torque is applied to said second strut through the active portion of the full range of motion of the joint; a plurality of aligned range of motion perforations provided in said housing about the periphery of said second gear and a pin for extension through a selected pair of said range of motion perforations for stopping said second strut at a selected point in the full range of motion of the joint, a strut perforation provided in said second strut and wherein said pin can be extended through a selected pair of said range of motion perforations and said strut perforation for locking said second strut at a selected point in the full range of motion of the joint; and a pair of cuff mounting frames provided in facing relationship on said first struts, respectively, a first cuff assembly mounted between said pair of cuff mounting frames, a pair of cuff mounting members provided in facing relationship on said second struts, respectively, and a second cuff assembly mounted between said pair of cuff mounting members.

* * * * *